(12) United States Patent
Kocaefe et al.

(10) Patent No.: US 10,281,421 B2
(45) Date of Patent: May 7, 2019

(54) METHOD FOR ANALYZING AN ANODE AND DEVICE THEREOF

(71) Applicant: UNIVERSITE DU QUEBEC A CHICOUTIMI, Chicoutimi (CA)

(72) Inventors: Duygu Kocaefe, Chicoutimi (CA); Dipankar Bhattacharyay, Chicoutimi (CA); Yasar Suleyman Kocaefe, Chicoutimi (CA)

(73) Assignee: UNIVERSITE DU QUEBEC A CHICOUTIMI, Chicoutimi (CA)

( * ) Notice: Subject to any disclaimer, the term of this patent is extended or adjusted under 35 U.S.C. 154(b) by 85 days.

(21) Appl. No.: 15/117,705

(22) PCT Filed: Feb. 13, 2015

(86) PCT No.: PCT/CA2015/050106
§ 371 (c)(1),
(2) Date: Aug. 9, 2016

(87) PCT Pub. No.: WO2015/120554
PCT Pub. Date: Aug. 20, 2015

(65) Prior Publication Data
US 2017/0089855 A1  Mar. 30, 2017

Related U.S. Application Data

(60) Provisional application No. 61/939,768, filed on Feb. 14, 2014.

(51) Int. Cl.
 *G01N 27/20* (2006.01)
 *G01R 31/01* (2006.01)
 *B65G 15/30* (2006.01)
(52) U.S. Cl.
 CPC ............. *G01N 27/20* (2013.01); *B65G 15/30* (2013.01); *G01R 31/01* (2013.01)

(58) Field of Classification Search
 CPC ......... G01N 27/20; B65G 15/30; G01R 31/01
 (Continued)

(56) References Cited

U.S. PATENT DOCUMENTS 3,735,253 A * 5/1973 Seger .................. G01N 27/041
 324/717
4,667,149 A * 5/1987 Cohen .................... G01N 25/18
 324/715
(Continued)

FOREIGN PATENT DOCUMENTS

CA 2138165 A1 6/1993
CA 2168556 8/1994
(Continued)

OTHER PUBLICATIONS

Chollier-Brym et al., "New Method for Representative Measurement of Anode Electrical Resistance", Light Metals 2012, pp. 1299-1302, Canada.

*Primary Examiner* — Patrick Assouad
*Assistant Examiner* — Sean Curtis
(74) *Attorney, Agent, or Firm* — Norton Rose Fulbright Canada LLP; Alexandre Daoust

(57) ABSTRACT

The method can include the steps of: providing a given current across each one of a plurality of current paths linking two opposite faces of the anode, the current paths being dispersed along a median plane located between the two opposite faces; measuring a voltage value independently across each one of a plurality of voltage paths linking the two opposite faces of the anode, each one of the plurality of voltage paths being positioned adjacent to a corresponding one of the current paths and forming a corresponding pair therewith, the path pairs thus being dispersed along the median plane; and processing an independent resistivity
(Continued)

value for each one of the path pairs based at least on its given current and its measured voltage value.

11 Claims, 7 Drawing Sheets

(58) Field of Classification Search
USPC .............................. 324/693, 71.1; 264/40.1
See application file for complete search history.

(56) References Cited

U.S. PATENT DOCUMENTS

| | | | |
|---|---|---|---|
| 4,670,110 A | 6/1987 | Withers et al. | |
| 5,138,269 A * | 8/1992 | Deutsch | G01N 27/20 324/713 |
| 5,473,248 A * | 12/1995 | Haldemann | G01N 27/20 204/401 |
| 6,932,891 B2 * | 8/2005 | Wigg | C23F 13/22 204/196.02 |
| 7,576,534 B2 * | 8/2009 | Audet | C25C 3/125 324/228 |
| 8,687,346 B2 * | 4/2014 | Gadkaree | H01G 11/26 361/502 |
| 9,416,458 B2 * | 8/2016 | Ziegler | G01N 27/041 |
| 2001/0045820 A1 * | 11/2001 | Kean | G01N 17/00 324/71.1 |
| 2005/0173250 A1 * | 8/2005 | Thies | C25D 17/10 205/83 |
| 2011/0292569 A1 * | 12/2011 | Gadkaree | H01G 11/26 361/502 |
| 2014/0183770 A1 * | 7/2014 | Ziegler | G01N 27/041 264/40.1 |
| 2017/0089855 A1 * | 3/2017 | Kocaefe | G01N 27/20 |

FOREIGN PATENT DOCUMENTS

| | | | | |
|---|---|---|---|---|
| CA | 2552145 A1 | 6/2005 | | |
| CA | 2604155 A1 | 10/2006 | | |
| CA | 2735815 A1 | 3/2010 | | |
| CA | 2939413 A1 * | 8/2015 | ............. | G01N 27/20 |
| CA | 2939413 A1 * | 8/2015 | ............. | G01N 27/20 |
| EP | 0212328 A1 | 3/1987 | | |
| WO | WO 2015120554 A1 * | 8/2015 | ............. | G01N 27/20 |
| WO | WO-2015120554 A1 * | 8/2015 | ............. | G01N 27/20 |

* cited by examiner

METHOD FOR ANALYZING AN ANODE AND DEVICE THEREOF

FIELD

The improvements generally relate to the field of aluminum production, and more particularly relate to the field of carbonaceous anodes largely used in aluminium smelters.

BACKGROUND

The industrial production of aluminum requires alumina ($Al_2O_3$) to be dissolved in molten cryolite ($Na_3AlF_6$) during the electrolysis. The electrolysis is performed by providing a direct current to the alumina and molten cryolite mix via a carbonaceous anode (typically very large—can exceed 1000 kg—and made from petroleum coke and coal tar pitch) and a graphite cathode. The aluminium smelters consume the carbonaceous anodes and this requires their replacement after 20-25 days.

Using anodes of good quality is important not only to provide a stable operation during the electrolysis process, but also to lower the electrical costs. Indeed, defects present in the structure of the anode can lead to the generation of undesirable heat which translates into a loss in energy efficiency (increased electrical energy consumption). Since the direct current involved in such smelters can currently reach up to 600 kA through the anode, reducing the loss in electrical energy consumption can be highly rewarding. Moreover, important fissures can lead to the loss of a relatively large portion of the anode at the bottom of the smelter, which can have a significant impact on plant productivity. Overall, the amount of anodes consumed also has an impact on the amount of greenhouse gases produced.

It was known to measure an average resistivity of a baked anode in conditions simulating the operation condition in order to obtain an indication of anode quality. The anode could be discarded if considered of unsatisfactory quality, in order to address the afore mentioned issues stemming from low quality anodes. Although the existing techniques are satisfactory to a certain degree, there remains room for improvement.

SUMMARY

The process of manufacturing anodes typically involves the production of a 'Green' anode consisting of solidified coke and pitch, and the 'baking' of this 'Green' anode to obtain a 'baked' anode.

To perform resistivity measurements, known techniques tend to simulate the conditions of use of a baked anode 10' during the electrolysis process. Indeed, a known techniques involve a relatively high direct current (above 250 A) to be provided from a stub hole 12' of an upper portion 14' of the anode to a lower portion 16' of the baked anode, as seen in FIG. 1. Once the baked anode has current flowing through it, voltage values are sequentially measured from the stub hole 12' to the lower portion 16' of the baked anode in order to measure the resistivity of the baked anode 10', which typically leaves some untested areas 18' of the baked anode, often referred to as dead spots.

Such resistivity measurements were not applied to 'green' anodes. In fact, green anodes are typically characterized by having a much higher resistivity value than baked anodes (by a factor of 30-50 times, for instance). Should this high resistivity be combined with high direct current for a certain period of time, the green anodes to heat up which can alter the pitch distribution leading to the modification of the original state of the green anodes, hence causing the misrepresentation of their actual state. More specifically, the induced heat is proportional to the square of the current amplitude and proportional to the duration of the test. The pitch binding the coke in green anodes can be affected by heat above 110-120° C. Some other materials which can be contained therein can be affected even by heat around 80° C. or lower.

Moreover, the known technique referred to above and shown in FIG. 1 has a limited field of view since the electrodes and the probes are disposed in the stub hole. Moreover, even if the device can detect a defect in its field of view 22' (such as a crack 20'), it did not allow localizing the crack since the multiple voltage values were averaged during the process. Moreover, a defect located outside the field of view or inside the dead spot 24') such as the crack 24' cannot be properly detected.

Accordingly, there is provided a method for measuring resistivity of an anode which uses an approach of using a plurality of distinct and interspaced measurement paths, which can perform a mapping of the resistivity of the anode rather than obtaining an averaged indication of resistivity in conditions of use. This new method can allow not only to detect the presence of a defect, but even obtaining an indication of a position and/or size of the defect and can also significantly reduce the size of blind spots if performed substantially along the entire opposite surfaces of the anodes.

Moreover, the method can be performed with relatively low currents such as less than 150 Amp, preferably less than 120 Amp, more preferably less than 50 Amp, and most preferably less than 10 Amp. Heat generation is a function of amperage, resistivity, and time. Henceforth, when performed at a sufficiently low amperage and for a sufficiently short period of time, the measures did not significantly alter green anodes and could thus be performed on green anodes, before baking, rather than being only performable on baked anodes. Accordingly, if a green anode is discarded based on the analysis method, the step of baking it is avoided, which is advantageous if compared to discarding the anode after baking. Using low currents can also be advantageous on baked anodes, such as from a security and energy consumption standpoint, for instance.

Moreover, by incorporating spring-loaded measurement electrical contacts to two supports provided on opposite sides of the anodes, all the contacts can be made with the anode in a simple mechanical step of bringing the supports closer to the anode, in opposition one with the other, and the tests can be performed in a surprisingly short period of time per anode, such as less than 5 minutes, preferably less than one minute, for instance.

Accordingly, there is provided a method for measuring resistivity of an anode which can determine a two-dimensional resistivity mapping across two opposites faces of the anode. Indeed, with a plurality of measurement paths across the anode, wherein each of the plurality of measurement paths are orthogonal relative to the two opposite faces and which are dispersed and distinct from one from the other along a median plane located between the two opposite faces, a given current value can be introduced through each of the measurement paths across the anode, and a voltage value can be measured between two ends of each of the measurement path. With those values, the resistivity can be processed for each of the measurements.

In accordance with one aspect, there is provided a method for measuring resistivity of an anode which has an increased field of view, thereby limiting the untested area of the anode to a great extent by providing a two-dimensional resistivity mapping based on the current and voltage values measured.

In accordance with another aspect, there is provided a method for analyzing an anode, the method comprising the steps of: providing a given current across each one of a plurality of current paths linking two opposite faces of the anode, the current paths being dispersed along a median plane located between the two opposite faces; measuring a voltage value independently across each one of a plurality of voltage paths linking the two opposite faces of the anode, each one of the plurality of voltage paths being positioned adjacent to a corresponding one of the current paths and forming a corresponding pair therewith, the path pairs thus being dispersed along the median plane; and processing an independent resistivity value for each one of the path pairs based at least on its given current and its measured voltage value.

In accordance with another aspect, there is provided a method for sequentially analyzing anodes, the method comprising: providing a sequence of anodes having at least a first anode and a second anode; positioning the first anode of the sequence of anodes at a measurement site; analyzing the first anode, said analysing comprising: providing a given current across each one of a plurality of current paths linking two opposite faces of the first anode, the current paths being dispersed along a median plane located between the two opposite faces; measuring a voltage value independently across each one of a plurality of voltage paths linking the two opposite faces of the first anode, each one of the plurality of voltage paths being positioned adjacent to a corresponding one of the current paths and forming a corresponding pair therewith, the path pairs thus being dispersed along the median plane; and processing an independent resistivity value for each one of the path pairs based at least on its given current and its measured voltage value; removing the first anode from the measurement site; positioning the second anode of the sequence of anodes at the measurement site; performing said analyzing on the second anode; and removing the second anode from the measurement site.

In accordance with another aspect, there is provided a device for analyzing an anode at positions spaced from one another, the device comprising: a plurality of current electrode pairs each having a first current electrode and a second current electrode connectable to at least one current generator, a plurality of voltage probe pairs each having a first voltage probe and a second voltage probe connected to one of the at least a voltmeter, each of the first current electrodes being mounted in a dispersed manner on a first planar support, face a second planar support, and are paired to an adjacent one of the first voltage probes being also mounted to the first planar support facing the second planar support; each of the second current electrodes being mounted on a second planar support, facing the first planar support, in normal alignment with corresponding ones of the first current electrodes in a manner to form a plurality of current paths across an anode when an anode is positioned in an analysis position between the first and second planar supports, the second current electrodes being paired to an adjacent one of the second voltage probes also being mounted to the second planar support and facing the first planar support.

In accordance with another aspect, there is provided a device for analyzing an anode at positions spaced from one another, the device comprising: at least a current generator; a plurality of current electrode pairs each having a first current electrode and a second current electrode connected to one of the at least a current generator, each of the first current electrodes to be disposed on a face of the anode and facing a corresponding one of the second current electrodes to be disposed on an opposite face of the anode thereby forming a plurality of paths across the anode, each of the plurality of current electrode pairs to be powered by a given current and forming a closed circuit via a corresponding one of the plurality of paths; at least a voltmeter; a plurality of voltage probe pairs each having a first voltage probe and a second voltage probe connected to one of the at least a voltmeter, each of the first voltage probes to be disposed in the vicinity of one of the first current electrodes on the face of the anode and facing a corresponding one of the second voltage probes to be disposed on the opposite face of the anode, at least a voltmeter adapted to measure a voltage value across a corresponding one of the plurality of paths; and a computer processing the plurality of resistivity values based at least on the given current value and the measured voltage value of each of the plurality of paths.

In accordance with another aspect, there is provided a system for analyzing a sequence of anodes comprising: a conveyor which is adapted to sequentially positioning anodes of the sequence of anodes at a measurement site, the sequence of anodes having at least a first anode and a second anode; a device for analysing an anode at the measurement site, the device having a first support having first current electrodes and first voltage probes protruding therefrom and towards the anode, the device having a second support having second current electrodes and second voltage probes protruding therefrom and towards the anode, the first and second supports adapted to providing a given current across first and second current electrodes forming a plurality of current paths linking two opposite faces of the anode, the current paths being dispersed along a median plane located between the two opposite faces; the first and second supports adapted to measuring a voltage value independently across first and second voltage probes forming a plurality of voltage paths linking the two opposite faces of the anode, each one of the plurality of voltage paths being positioned adjacent to a corresponding one of the current paths and forming a corresponding pair therewith, the path pairs thus being dispersed along the median plane; and processing an independent resistivity value for each one of the path pairs based at least on its given current and its measured voltage value; and a computer in communication with the device for determining the independent resistivity value for each one of the path pairs of the sequence of anodes.

Many further features and combinations thereof concerning the present improvements will appear to those skilled in the art following a reading of the instant disclosure.

DESCRIPTION OF THE FIGURES

In the figures.

DETAILED DESCRIPTION

Figure 1:
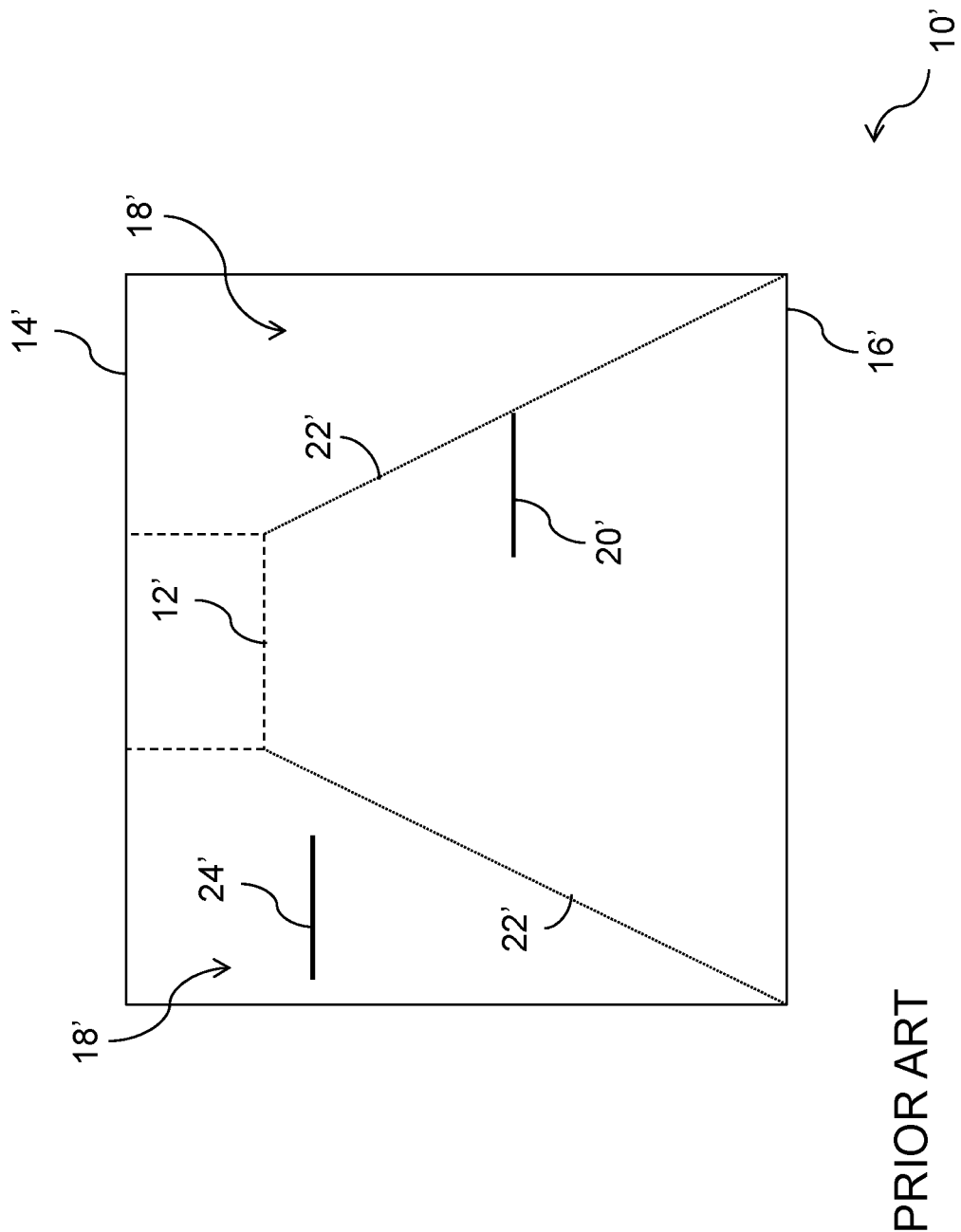
FIG. 1 is a schematic view of an example of an anode being measured with a resistivity measuring device of the prior art.
Figure 2:
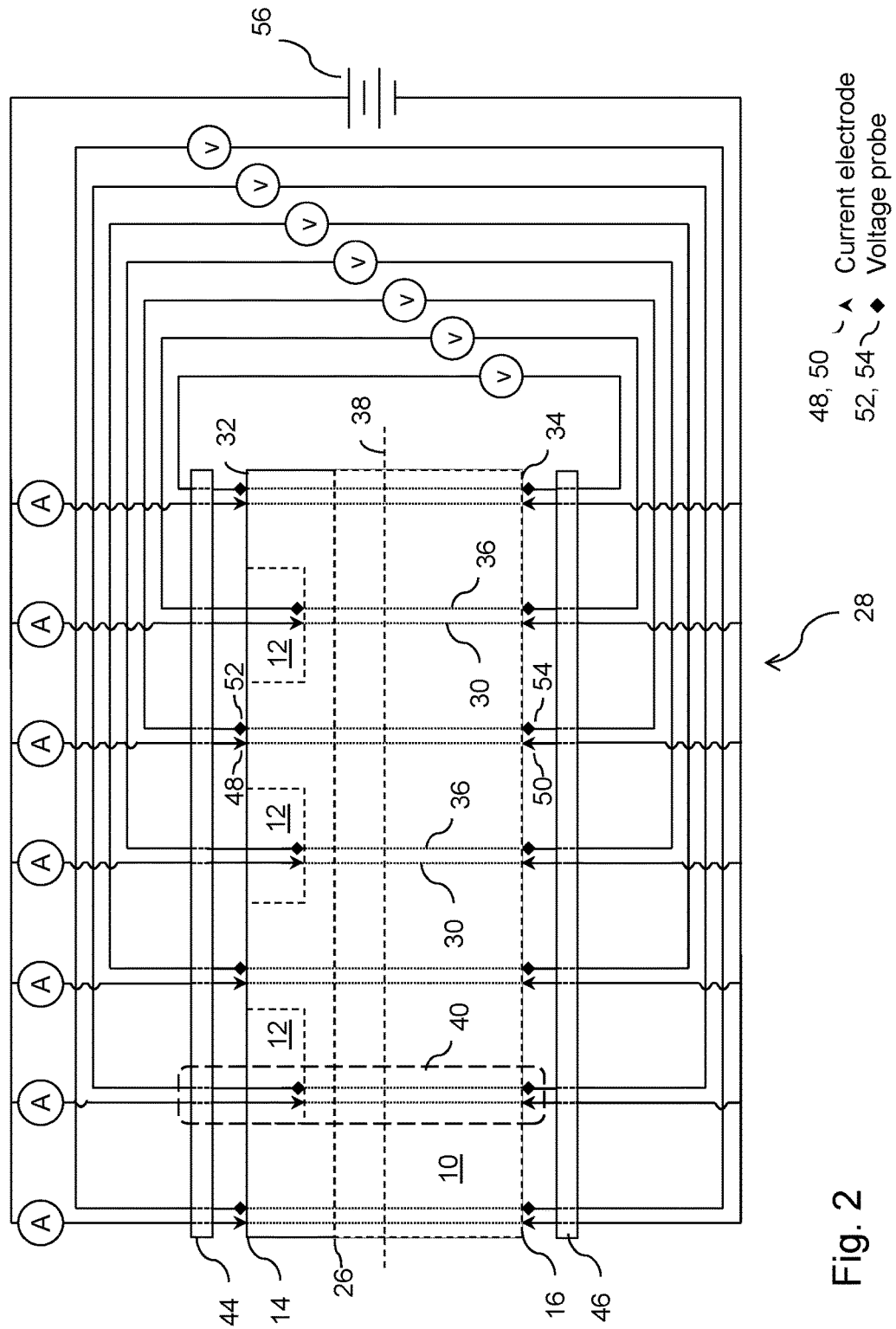
FIG. 2 is a schematic view showing a first example of a device for analyzing an anode.

An example anode 10 is shown in FIG. 2. The anode has an upper portion 14 and a lower portion 16. The upper portion 14 has an exemplary number of three stub holes which are used to apply a high current via electrical buses (not shown). Moreover, the anode 10 has bubbles escaping cavities (slots) 26 along an axis of the cavity which allow carbon dioxide and carbon monoxide, which is created during the electrolysis process, to escape from the lower portion of the anode. An anode 10 such as shown in FIG. 2 can weigh over 1000 kg, which can impose specific handling issues either during displacement or analysis.

A first example of a device 28 for analyzing an anode can provide a given current across each one of a plurality of current paths 30 which links two opposite faces 32, 34 of the anode. The plurality of current paths 30 can be located all over the two opposite faces 32, 34 of the anode 10. Subsequently, the device 28 can measure a voltage value across each one of a plurality of voltage paths 36 linking, in an orthogonal manner, the two opposite faces 32, 34 of the anode 10 along a median plane 38 of the anode 10. Each one of the plurality of voltage paths 36 can form a path pairs 40 with a corresponding one of the plurality of current paths 30 that is positioned in the vicinity thereof. Therefore, each current path 30 has its associated voltage path 36 nearby which allows a current value and a voltage value to be measured across a shared region 42 of the anode. Subsequently, the device 28 can process a resistivity value for each one of the path pairs 40 (or shared region 42) based at least on its given current and its measured voltage value, and determine a two-dimensional resistivity map of the anode 10 based on the resistivity values measured. Indeed, other parameters than the measured voltage value and the measured current value intervene when calculating the resistivity.

It is noted that the resistivity ρ at a position P can be computed by:

$$\rho = (V_{mes}/I_{mes}) \cdot (A_{avg}/h_{avg}); \quad (1)$$

where $V_{mes}$ is the voltage measured across a voltage path P, $I_{mes}$ is the current measured across the corresponding current path P, $A_{avg}$ is the area of the anode transverse to the path pairs and $h_{avg}$ is the height of the anode at the position P. Moreover, it is noted that even if the current path are shown to be rectilinear, the exact paths of the individual electrons will deviate slightly especially if inhomogeneous portions of the anode are crossed.

The discovery of a flaw in an anode before baking can help avoid baking it uselessly in some cases. Moreover, the current electrodes can be independent and dispersed across the median plane of the anode, in a manner avoiding blind spots while being subjected to a low current. Therefore, defects or inhomogeneities which are located away from the stub holes can be identified. Furthermore, the two-dimensional resistivity map can allow a skilled technician or even a computer-implemented program to identify and locate defects present in the anode. Moreover, the device for analyzing the anode can be used along one, two, or three orthogonal median planes of the anode, and can thus be used not only in obtaining a two-dimensional resistivity map, but even further to obtain a three-dimensional resistivity map which can determine features of a defect with significant detail.

Still referring to FIG. 2, the device has a first support 44 which is disposed on the face 32 of the anode, and a second support 46 which is disposed on the opposite face 34 of the anode 10. In this embodiment, both supports are provided in the form of plates. The face 32 and the opposite face 34 can be any suitable one of the pairs of opposite faces that an anode 10 can have. The device is not limited only to measurement across the upper portion 14 and the lower portion 16 of the anode.

First current electrodes 48 and first voltage probes 52 protrude from the first support 44 which facilitates an electrical contact with a surface of the anode 10. In the same manner, the second current electrodes 50 and the second voltage probes 54 protrude from the second support 46. The electrodes 48, 50 and the probes 52, 54 are electrically isolated from their respective first and second support 44, 46. Alternatively and/or concurrently, the first and second supports 44, 46 can be made of an insulating material. As it may be appreciated by one skilled in the art, each of the first and second current electrodes 48, 50 and each of the first and second voltage probes 52, 54 can be spring loaded in order to exert a constant pressure on the anode 10 to be measured. This can circumvent false contacts in the event where the surface of the anode is rough.

Since the device measures multiple voltage values and multiple current values, the device can be made using many combinations of voltmeters, ammeters and/or current generators. For the sake of simplicity, only few combinations are shown in the figures, however many more combinations can appear obvious for one skilled in the art.

The exact value of the current used across each path can vary in different applications. When addressing a baked anode, the resistivity is low and it can be convenient to use a current amplitude of above 5A to allow the use of common, low-cost measuring equipment. When addressing a green anode, the resistivity can be higher by an order of magnitude or even more. Henceforth, a current amplitude of 1 or 2 A can be sufficient to establish a satisfactory voltage across the path to allow the use of measuring equipment commonly available at the time of filing this specification. In both cases, it can be preferred to maintain the current amplitude below 10 A for similar reasons.

Figure 3:
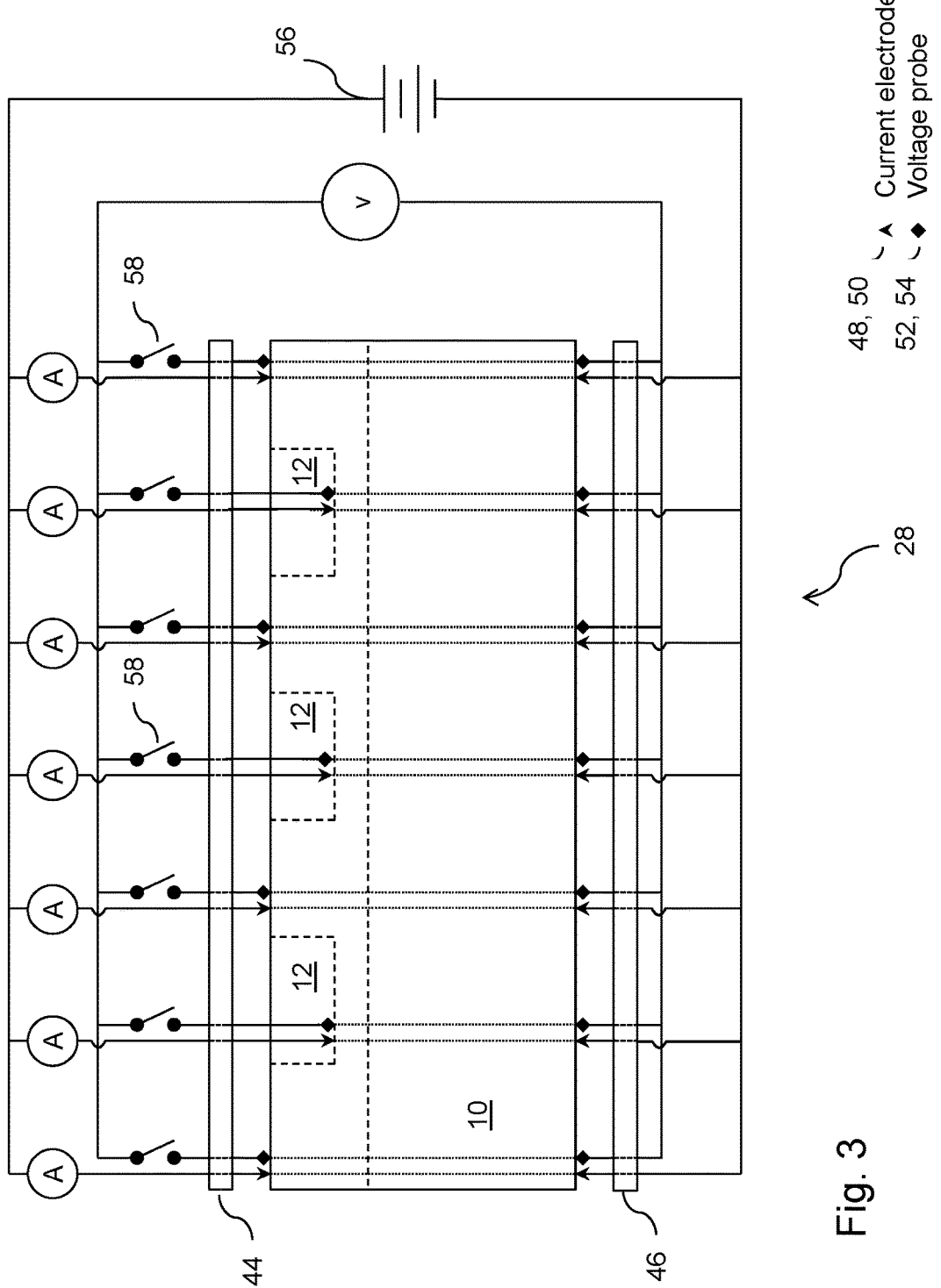
FIG. 3 is a schematic view showing a second example of a device for analyzing an anode.

More specifically, FIG. 2 shows a first example where the device has multiple and independent voltmeters V and a single current generator 56 powering the branches leading to the first current electrodes, while FIG. 3 shows a second example where the device has a single voltmeter V using electrical switches 58 to measure the voltage across each one of the voltage paths, a single current generator 56 powering the branches leading to the current electrodes. Moreover, the device 28 can have electronics which differs from the first and second examples. Indeed, multiple and independent voltmeters V and multiple current generators for powering respectively multiple branches leading to the first electrodes. Also, the device can have a single voltmeter and multiple current generators for powering respectively multiple branches leading to the first electrodes.

It has to be noted that the given current may be obtained either by setting the current generator to the given current or by measuring the given current with an ammeter. Accordingly, one could set the current generator to five amperes, for instance, and base the resistivity calculations on this value instead of measuring the instantaneous current flowing across the circuit. However, measuring the instantaneous current flowing across the current paths may provide more relevant results. In embodiments which incorporate a single current generator, an ammeter can be positioned right next to current generator, or multiple ammeters can be independently positioned right next to each of the current electrodes. In embodiments incorporating multiple current generators, an ammeter for each one of the multiple current generators can be provided right next to its corresponding current generator. The voltmeters used can be a high-impedance voltmeter draining only a low current and exhibiting a very high resistance.

Figure 4:
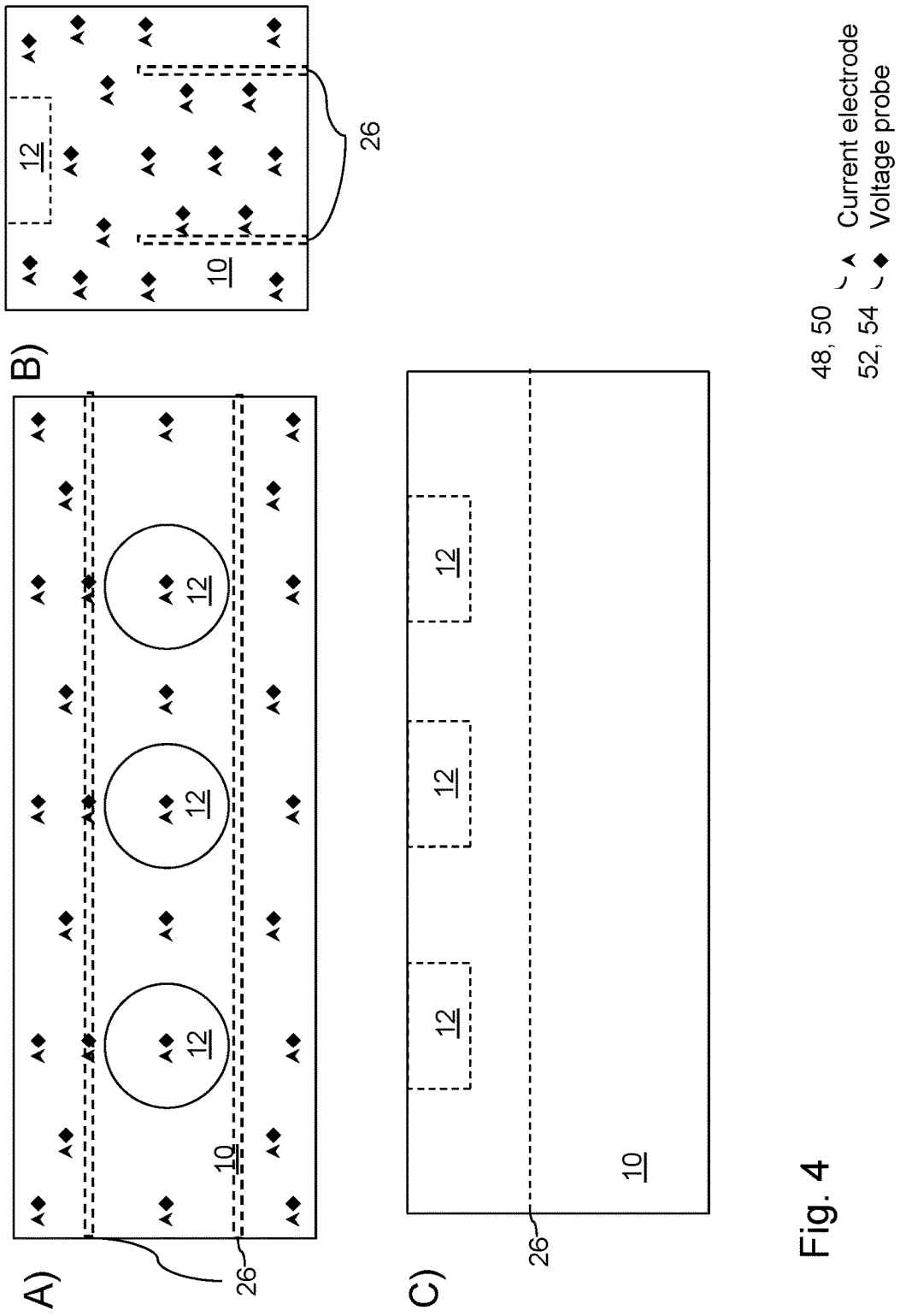
FIG. 4A is a schematic view showing a top view of an anode with an alternate example of current electrodes and voltage probes configuration.
FIG. 4B is a schematic view showing a lateral view of an anode with an alternate example of current electrodes and voltage probes configuration.
FIG. 4C is a schematic view showing a side view of an anode.

FIGS. 4 show different examples of how opposite faces of the anode can be sampled in order to obtain the two-dimensional resistivity mapping. For instance, FIG. 4A shows a top view of an anode 10 where pairs of first current electrodes 48 and first voltage probes 52 are provided in the stub holes 12, and out of the stub holes. FIG. 4B shows a lateral view of the anode 10 where pairs of first current electrodes 48 and first voltage probes 52 are provided in a dispersed manner on a face of the anode 10. In this example, the stub hole 12 is avoided since it may lead to an increased resistivity measurement due to the air across the current and the voltage paths. In the same manner, FIG. 4C shows a side view of the anode 10. It will be noted here that pairs of first current electrodes and first voltage probes can also be provided in a dispersed manner on the side faces of the anode, which can particularly be useful when applied to anodes having no slots 26. As shown in FIG. 4, a pattern of first current electrodes 48 and first voltage probes 52 is not limited to regular arrays.

Figure 5:
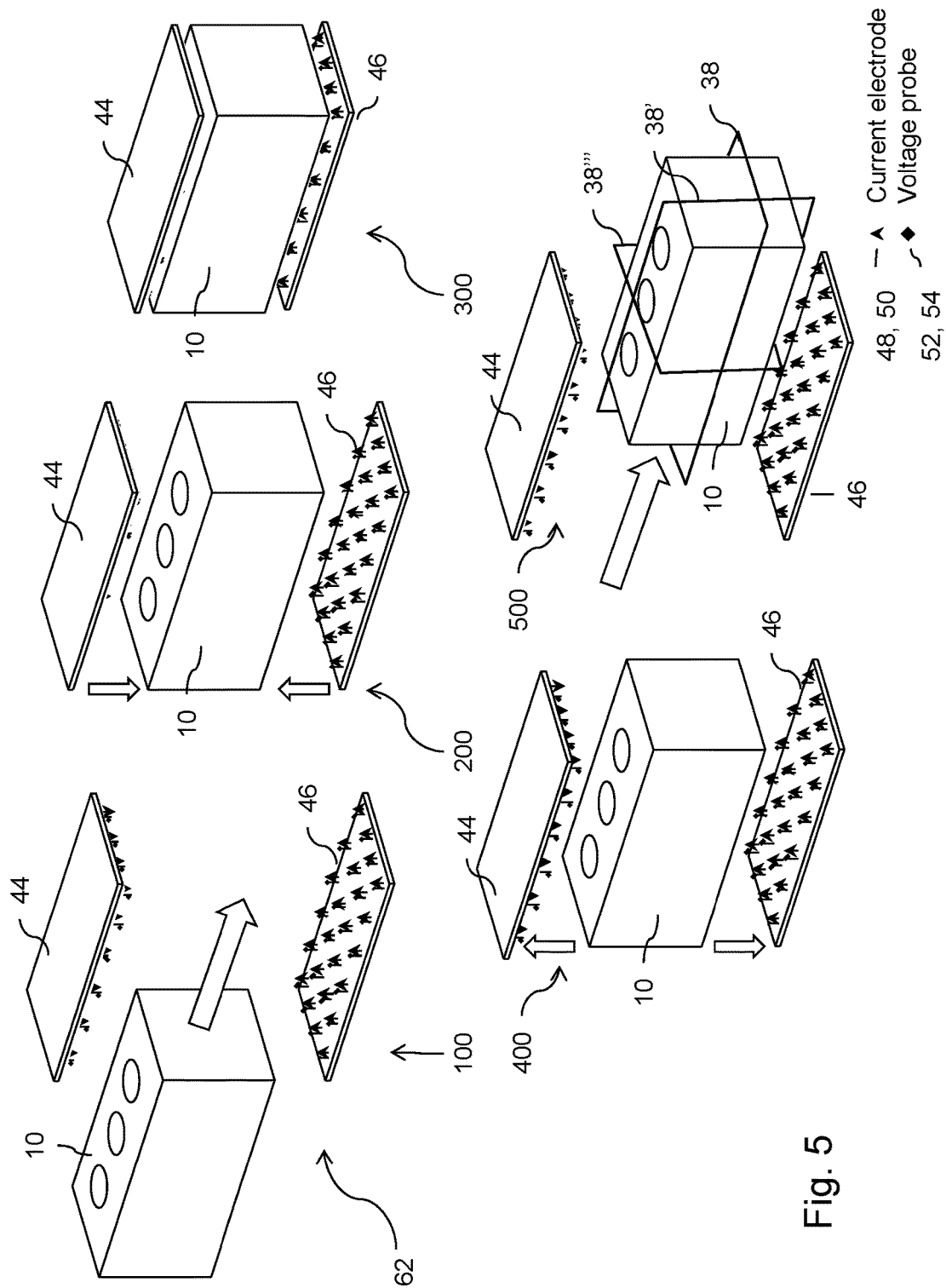
FIG. 5 is a schematic view showing a system implementing a device for analyzing an anode.

FIG. 5 shows a system 62 for analyzing a sequence of anodes having at least a first anode and a second anode. In this example, the system 62 can measure a two-dimensional resistivity mapping (or only resistivity values) in five different steps. In the step 100, until the anode 10 reaches the first and second supports 44, 46, the anode is conveyed using a conveyor (not shown) having a meshed belt, for instance. Once the anode 10 is at a measurement site 64 place between the two supports 44, 46, the first support 44 can be lowered and the second support 46 can be elevated in step 200. In this step, the first current electrodes 48 and the first voltage probes 52 make an electrical contact with the upper portion of the anode. Concurrently, the second current electrodes 50 and the second voltage probes 54 can pass through the mesh belt and subsequently make an electrical contact with the lower portion of the anode 10. Once the current electrodes and the voltage probes are in contact with the anode 10, the voltage values and current values are measured in step 300. Once the two-dimensional resistivity map has been processed, the first and second supports 44, 46 can be distanced from the anode 10 in step 400. Finally, the anode 10 can be conveyed away from the device in step 500 which allows another anode to be measured shortly right after (not shown). It has to be noted that the five steps can be completed in less than a minute, which allows for a large number of anodes per hour to be tested with such a system.

In another embodiment, the device for analyzing the anode can be used upon another median plane of the anode. More specifically, the anode can have three orthogonal median planes 38, 38' and 38" (shown in FIG. 5, step 500). As the device can be used on only one of the median planes to provide a two-dimensional resistivity mapping, it can also be used on another median plane to obtain a three-dimensional resistivity mapping of the anode. With such a three-dimensional resistivity mapping, one can identify a position (x, y, z) where the defect is located in the anode.

Although the system 62 for analyzing a sequence of anodes of FIG. 5 is shown to analyze the anode 10 from the upper portion and the lower portion of the anode, the system is not limited to such a limitation. Indeed, two lateral faces (perpendicular with the faces shown in FIG. 5) of the anode could be tested with the system of FIG. 5 if the first and second supports are both rotated by ninety degrees, for instance. In such an embodiment, the belt of the conveyor can be flat since the second current electrodes and the second voltage probes may not need to pass therethrough.

EXAMPLE

Figure 6:
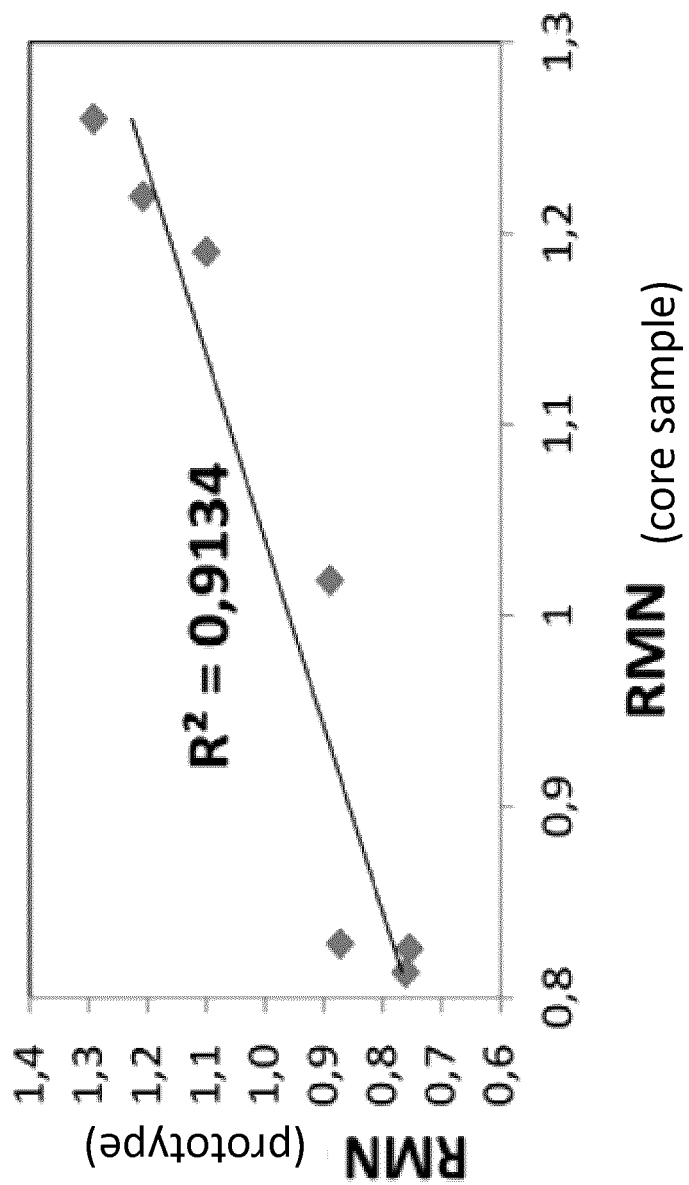
FIGS. 6 and 7 are graphs showing experimental data point comparisons.
Figure 7:
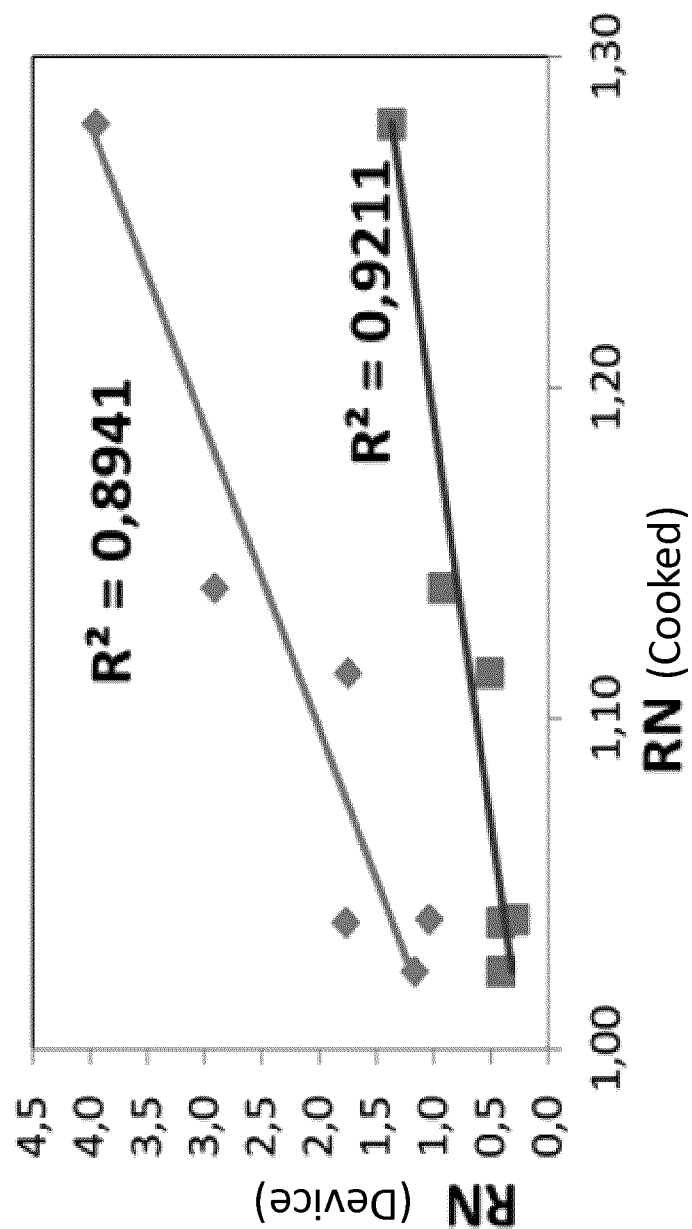

A static, low-cost prototype was made to validate the concept and its applicability to the industrial control of anode quality. This prototype was used to measure the distribution of the electric resistivity in more than thirty 'green' industrial anodes and the average resistivity was then calculated for each anode. Then, the anodes were separated into two groups. The anodes of the first group (about 25% of the tested anodes) were core sampled in the green state at a number of positions, and the electric resistivity of these samples were measured using a classic 4-point method. The average values were determined for each anode and compared to the measured results. The comparison of these two series of data (shown here as normalized average resistivities—RMN) is presented at FIG. 6, where the correlation is good ($R^2$=0.91) between the measures taken with the prototype and those obtained with the classic method. The anodes of the second group (about 75% of the tested anodes) were cooked. With the prototype, we measured the electrical resistivity distribution in each of these cooked anodes. Afterwards, there were core sampled at a number of positions in a manner similar to that conducted with those of the first group and referred to above; the electrical resistivity of the core samples was measured using the 4-point method. The resistivities measured with the prototype were compared with those of the core samples obtained at corresponding positions. FIG. 7 shows the results for one anode where normalized resistivities (RN) measured with the device are compared with normalized resistivity experimentally measured both for the cooked status (diamond set of data points) and for green status (square set of data points). Here also, a reasonably well correlated tendency is shown for the comparison between the prototype results and those of the core samples. The correlation coefficient ($R^2$) for the case of baked anodes measured with the prototype vs. baked anode core sample measured varies between 0.7 and 0.95 depending on the exact position, averaging at 0.81±0.07; and for the case of green anodes measured with the prototype vs. baked anode core sample measured varies between 0.54 and 0.95 depending on the exact position, averaging at 0.74±0.08). A next step is to make a statistic prototype and to focus tests on the automated design where the tests will be taken on static anodes externally from the production line and to establish conditions to reject a green anode.

As can be understood, the examples described above and illustrated are intended to be exemplary only. The scope is indicated by the appended claims.

What is claimed is:

1. A method for analyzing an anode, the method comprising the steps of:
    contacting a plurality of current injection electrodes on a
        first one of two opposite faces of the anode and a plurality of current reception electrodes on a second one of the two opposite faces of the anode, a number of the plurality of current injection electrodes being equivalent to a number of the plurality of current reception electrodes, the current injection electrodes forming a plurality of current paths with corresponding current reception electrodes, the plurality of current paths extending across the anode, linking the two opposite faces of the anode to one another, and being dispersed along a median plane located between the two opposite faces;

using the current injection electrodes and the current reception electrodes, injecting a given current across each one of the plurality of current paths;

measuring a voltage value independently across each one of a plurality of voltage paths extending across the anode and linking the two opposite faces of the anode, each one of the plurality of voltage paths being positioned adjacent to a corresponding one of the current paths and forming a corresponding pair therewith; and processing an independent resistivity value for each one of the path pairs based at least on its given current and its measured voltage value.

2. The method of claim 1, wherein the anode is a green anode and the analysis is performed before baking.

3. The method of claim 1, wherein the path pairs are orthogonal relative to the median plane of the anode, the method further comprising obtaining a two-dimensional resistivity mapping of the anode.

4. The method of claim 3, wherein the path pairs are evenly dispersed one from the other and form a regular array across the median plane.

5. The method of claim 1, wherein said providing further comprises measuring a current value independently across each one of the plurality of current paths.

6. The method of claim 3 further comprising effecting the steps of said contacting, said injecting, said measuring and said processing upon another median plane, and further comprising obtaining a three-dimensional resistivity mapping of the anode based on the values obtained with said effecting.

7. The method of claim 1, wherein the given current is less than 120 amperes, preferably less than 50 amperes, most preferably less than 10 amperes.

8. The method of claim 1 wherein said processing further comprises comparing the resistivity value of each one of the path pairs with a threshold value, further comprising determining the presence of a defect associated with the position of a path pair when the associated resistivity value exceeds the threshold value.

9. The method of claim 8, wherein said determining further comprises determining a location of the defect based on the position of the path pair.

10. The method of claim 8, further comprising associating a defect to a plurality of adjacent path pair positions and obtaining an indication of a size of the defect based on the associated path pair positions.

11. The method of claim 2 wherein the given current is selected as a function of a period of time of said measuring and of the resistivity of the anode in order to avoid temperatures above 110° C., preferably temperatures above 80° C., most preferably temperatures above 50° C.

* * * * *